US006500792B2

(12) United States Patent
Riesgraf et al.

(10) Patent No.: US 6,500,792 B2
(45) Date of Patent: Dec. 31, 2002

(54) SOLID COMPOSITION COMPRISING VITAMIN E ACETATE

(75) Inventors: Diane Riesgraf, Hillsborough; Nadia Soliman, East Brunswick; Zeenat Nabi, Cranbury, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/769,077

(22) Filed: Jan. 25, 2001

(65) Prior Publication Data

US 2002/0142925 A1 Oct. 3, 2002

(51) Int. Cl.[7] .................................................. A61K 7/50

(52) U.S. Cl. ....................... 510/152; 510/141; 510/155; 510/504

(58) Field of Search ................................ 510/141, 152, 510/155, 504

(56) References Cited

U.S. PATENT DOCUMENTS

| | | | | |
|---|---|---|---|---|
| 4,954,332 | A | 9/1990 | Bissett et al. | 424/59 |
| 5,011,681 | A | 4/1991 | Ciotti et al. | 424/81 |
| 5,627,149 | A | 5/1997 | Patel | 510/125 |
| 5,955,409 | A | 9/1999 | Farrell et al. | 510/141 |
| 6,036,946 | A | 3/2000 | Greene | 424/59 |
| 6,057,275 | A | 5/2000 | Fair et al. | 510/151 |
| 6,153,208 | A | 11/2000 | McAtee et al. | 424/402 |
| 6,218,348 | B1 | 4/2001 | Aronson et al. | 510/153 |

FOREIGN PATENT DOCUMENTS

| | | |
|---|---|---|
| WO | 9918928 | 4/1999 |

*Primary Examiner*—Necholus Ogden
(74) *Attorney, Agent, or Firm*—Martin D. Barancik

(57) ABSTRACT

A solid cleansing composition comprising a. About 1 to about 90 wt. % soap,
b. About 0.02 to about 2.0 wt. % of a Vitamin E precursor or mixture thereof,
c. A Vitamin E precursor deposition effective amount of a cationic deposition polymer or mixture thereof, and
d. From zero to the essential absence of Vitamin E.

5 Claims, No Drawings

SOLID COMPOSITION COMPRISING VITAMIN E ACETATE

BACKGROUND OF THE INVENTION

Antioxidants are known to be useful in combating various conditions of the body associated with the activity of free radicals. Antioxidants quench free radicals so they can not interact with the body's systems.

Among the most well known antioxidants are the vitamins, particularly Vitamin E and its precursors. When used in topical compositions, particularly cleansing compositions, the Vitamin E and its precursors can have difficulty with deposition on skin.

We have now discovered a soap bar, which can deposit significant levels of Vitamin E precursor as well as other vitamins and their precursor(s).

SUMMARY OF THE INVENTION

In accordance with the invention, there is a solid cleansing composition comprising:

a. About 1 to about 90 wt. % soap, b. About 0.01 to about 2.0 wt. % of a Vitamin E precursor or mixture thereof, c. Vitamin E precursor deposition effective amount of a cationic deposition polymer or mixture thereof and, d. From zero to the essential absence of Vitamin E.

DETAILED DESCRIPTION OF THE INVENTION

Soap, the long chain alkyl carboxylate salt, can be present in the solid composition in quantities of from about 1 to about 90 wt. %, desirably about 5 to about 90 wt. %, with desirable minimum of at least about 10, 20, 30, 40, 50 or 60 wt. %. The higher quantities, about 60 to about 90 wt. % are found in the traditional soap bar. Intermediate quantities of soap such as about 40 to about 70 wt. % are generally found in a combination bar while lower quantities of soap, about 10 to about 40 wt. % are generally found in a syndet bar. Preferred salts are the soaps prepared from the alkali metals, such as sodium and potassium and ammonia such as ammonium or substituted ammonium.

Other surfactants can be present or omitted as well. Examples of these surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixture of ethoxylated alkyl sulfates and the like.

Alkyl chains for these surfactants are about $C_8$–$C_{22}$, preferably about $C_{10}$–$C_{18}$, more preferably about $C_{12}$–$C_{18}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (i.e., tallow or coconut oil alcohols) and 1 to 2 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

$$R^2\text{—}\overset{\displaystyle (R3)x \atop |}{Y^{(+)}}\text{—}CH_2\text{—}R^4\text{—}X^{(-)}$$

Wherein $R^2$contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-dimethyl-N-hexadecylammonio)propane-1-sulfonate; 3-(N,N-dimethyl-N-hyxadecylammonio)-2-hydroxypropane-1-sulfonate; 4-N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives to aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium dodecylaminoproprionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary $4^{th}$ Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.
2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000 are satisfactory.
3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).
4. Long chain tertiary amine oxide corresponding to the following general formula:

$$R_1R_2R_3N\rightarrow 0$$

wherein $R_1$ contains an alkyl, alkenyl or monohdroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxypropyl radicals. The arrow in the formula is a conventional representation of a semipolar bond. Examples of amine oxides suitable for use in this invention include:

Dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P\rightarrow 0$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: Dodecyldimethylphosphine oxide, tetradecylmethylethylphosphine oxide, 3,6,9-trioxaoctadecyidimethylphosphine oxide, cetyldimethylphosphine oxide, 3-dodecoxy-w-hydroxypropyldi(2-hydroxyethyl)phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alky, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecylmethyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide; 3 methoxytridecylmethyl sulfoxide, 3-hydroxytridecyl methyl sulfoxide, 3-hydroxy-4-dodecoxybutyl methyl sulfoxide.
7. Alkylated polyglycosides wherein the alkyl group is from abut 8 to about 20 carbon atoms, preferably about 10 to about 18 carbon atoms and the degree of polymerization of the glycoside is from about 1 to about 3, preferably about 1.3 to abut 2.0.

Quantities of these surfactants can vary but which can be generally included in the solid formulation are at least about 1, 2, 5, 10, 20 or about 30 wt. % up to about 60 wt. % as a maximum.

Water is present in the solid formulation, preferably a bar in quantities of from about 5 to about 30 wt. % of the solid. Desirable quantities are from about 7 to about 30 wt. %, and about 9 to about 25 wt. %.

Examples of Vitamin E precursor or mixture thereof include esters of vitamin wherein the acid has from 2 to about 20 carbon atoms, including Vitamin E acetate, proprionate, hexanoate, cocoate, palmitate, stearate, and the like. Other vitamin antioxidant(s) and or their precursors such as Vitamin A and Vitamin C and mixtures thereof of each or both can also be present in the formulation. Precursor of Vitamin A include esters having about 2 to about 20 carbon atoms including the myristate and palmitate. Vitamin C precursors include the cholesteryl and the sodium ascorbyl phosphate salt.

Quantities of Vitamin E precursor can be at a minimum of about 0.01, 0.02 or about 0.05 wt. % of the formulation, desirably at least about 0.1 or 0.2 wt. %. Maximum quantities of Vitamin E precursor are dependent upon the level of skin toxicity but are primarily dependent upon the plateau level of observed activity for the Vitamin E effect. Generally, no more than about 2 or about 1.5 wt. % should be employed.

With respect to Vitamin C and A and their precursors, minimum quantities are from about 0.01 or 0.02 or 0.05 wt. % of the formulation. Maximum quantities are generally no more than about 2 or about 1.5 wt. %.

An important part of the solid formulation are Vitamin E precursor deposition effective amounts of cationic polymer. Examples of such a deposition polymer include but are not limited to the following groups:

(I) cationic polysaccharides;

(II) cationic copolymers of saccharides and synthetic cationic monomers, and (III) synthetic polymers selected from the group consisting of:

(a) cationic polyalkylene imines (b) cationic ethoxy polyalkylene imines (c) cationic poly[N-[3-(dimethylammonio)propyl]-N' [3-(ethyleneoxyethylene dimethylammonio)propyl] urea dichloride]

(d) in general a polymer having a quaternary ammonium or substituted ammonium ion.

The cationic polysaccharide class encompasses those polymers based on a 5 or 6 carbon sugars and derivatives, which have been made cationic by engrafting of cationic moieties onto the polysaccharide backbone. They may be composed of one type of sugar or of more than one type, i.e. copolymers of the above derivatives and cationic materials. The monomers may be in straight chain or branched chain geometric arrangements. Cationic polysaccharide polymers include the following: Cationic celluloses and hydroxyethyl celluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on galactomannan copolymer known as guar gum obtained from the endosperm of the guar bean.

Specific examples of members of the cationic polysaccharide class include the cationic hydroxyethyl cellulose JR 400 made by Union Carbide Corporation; the cationic starches Stalok® 100, 200, 300, and 400 made by Staley, Inc.; the cationic galactomannans based on guar gum of the Galactasol 800 series by Henkel, Inc. and the Jaguar Series by Celanese Corporation.

The cationic copolymers of saccharides and synthetic cationic monomers useful in the present invention encompass those containing the following saccharides: Glucose, galactose, mannose, arabinose, xylose, fucose, fructose, glucosamine, galactosamine, glucuronic acid, galacturonic acid, and 5 or 6 membered rinse polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α; 1,4-β; 1,3-α; 1,3-β and 1,6 linkages. The synthetic cationic monomers for use in these copolymers can include dimethyldiallylammonium chloride, dimethylaminoethylmethyacrylate, diethyldiallyl ammonium chloride, N,N-diallyl,N-N-dialklyl ammonium halides, and the like. A preferred cationic polymer is Polyquaternium 7 prepared with dimethyldiallylammonium chloride and acrylamide monomers.

Examples of members of the class of copolymers of saccharides and synthetic cationic monomers include those composed of cellulose derivatives (e.g. hydroxyethyl cellulose) and N,N-diallyl,N-N-dialkyl ammonium chloride available from National Starch Corporation under the tradename Celquat.

Further cationic synthetic polymers useful in the present invention are cationic polyalkylene imines, ethoxypolyalkelene imines, and poly {N-[3-(dimethylammonio)-propyl]-N'-[3-(ethyleneoxyethylene dimethylammoniumo)propyl] urea dichloride] the latter of which is available from Miranol Chemical Company, Inc. under the trademark of Miranol A-15, CAS Reg. No. 68555-336-2. Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anydroglucose unit to about 0.80 per anydroglucose unit with the substituent cationic group being the adduct of 2,3-epoxypropyl-trimethyl ammonium chloride to the natural polysaccharide backbone. Examples are JAGUAR C-4-S, C-15 and C-27 sold by Celanese Corporation, which trade literature reports have 1% viscosities of from 125 cps to about 3500±500 cps.

Still further examples of cationic polymers include the polymerized materials such as certain quaternary ammonium salts, copolymers of various materials such as hydroxyethyl cellulose and dialkyldimethyl ammonium chloride, acrylamide and beta methacryloxyethyl trimethyl ammonium methosulfate, the quaternary ammonium salt of methyl and stearyl dimethylaminoethyl methacrylate quaternized with dimethyl sulfate, quaternary ammonium polymer formed by the reaction of diethyl sulfate, a copolymer of vinylpyrrolidone and dimethyl aminoethylmethacrylate, quaternized quars and guar gums and the like. Exemplary of cationic polymers which can be used to make the complexes of this invention include, as disclosed in the CTFA International Cosmetic Ingredient Dictionary (fourth Edition, 1991, pages 461–464); Polyquaternium -1, -2, -4 (a copolymer of hydroxyethylcellulose and diallyldimethyl ammonium chloride), -5 (the copolymer of acrylamide and beta-methacrylyloxyethyl trimethyl ammonium methosulfate), -6 (a polymer of dimethyl diallyl ammonium chloride), -7 (the polymeric quaternary ammonium salt of acrylamide and dimethyl diallyl ammonium chloride monomers), -8 (the polymeric quaternary ammonium salt of methyl and stearyl dimethylaminoethyl methacrylate quaternized with dimethyl sulfate), -9 (the polymeric quaternary ammonium salt of polydimethylaminoethyl methacrylate quaternized with methyl bromide), -10 (a polymeric quaternary ammonium salt of hydroxyethyl cellulose reacted with a trimethyl ammonium substituted epoxide), -11 (a quaternary ammonium polymer formed by the reaction of diethyl sulfate and a copolymer of vinyl pyrrolidone and dimethyl aminoethyl methacrylate), -12 (a polymeric quaternary ammonium salt prepared by the reaction of ethyl methacrylate/aietyl methacrylate/diethylaminoethyl methacrylate copolymer with dimethyl sulfate), -13 (apolymeric quaternary ammonium salt prepared by the reaction of ethyl methacrylate/oleyl methacrylateldiethylaminoethyl methacrylate copolymer with dimethyl sulfate), -14, -15 (the copolymer of acrylamide and betamethacrylyloxyethyl trimethyl ammonium chloride), -16 (a polymeric quaternary ammonium salt formed from methylvinylimidazolium chloride and vinyl pyrrolidone), -17, -18, -19 (polymeric quaternary ammonium salt prepared by the reaction of polyvinyl alcohol with 2,3-epoxy-propylamine), -20 (the polymeric quaternary ammonium salt prepared by the reaction of polyvinyl octadecyl ether with 2,3-epoxypropylamine), -22, -24 a polymeric quaternary ammonium salt of hydroxyethyl cellulose reacted with a lauryl dimethyl ammonium substituted epoxide), -27 (the block copolymer formed by the reaction of Polyquaternium-2 (q.v.) with Polyquaternium-17 (q.v.)), -28, -29 (is Chitosan (q.v.) that has been reacted with propylene oxide and quaternized with epichlorohydrin), and -30.

Quantities of such a cationic polymer are generally a minimum of about 0.01, 0.02 or 0.05 wt. % of the formulation. Generally, the maximum quantity is no more than about 1.0 or about 0.8 wt. % of the formulation.

As stated previously, there is an absence or an essential absence of Vitamin E present in the formulation. No more than about 0.05 or about 0.04 wt. % of the formulation should be present as Vitamin E, desirably 0 wt. %.

The cationic polymer brings about substantially increased deposition of the Vitamin E precursor onto the skin during the skin cleansing process utilizing the solid rinse off formulation, usually in the general physical form of a bar. Such increased deposition allows the effects of the vitamins, particularly Vitamin E, to assert itself since it is present on the skin in significant quantities for a longer period of time. Protection of the skin particularly in the area of quenching or neutralizing free radicals can occur because of the deposition. Replenishment of and addition to Vitamin E skin levels can also occur even after reduction of Vitamin E skin level following exposure to sun.

The following components can also be present in the solid formulation, for example: Antibacterials, triclosan and triclocarbanilide, preservatives, fragrances, colorants, striation producing materials, emollients, structurants, UV protectants and the like. Of particular significance are certain materials such as mineral oil, petrolatum, silicone and the like.

Below are examples of the invention together with comparison examples to show the substantially enhanced benefits of this new solid formulation.

The formulations are prepared by standard addition techniques.

EXAMPLE 1

A test was conducted to quantify the deposition of Vitamin E acetate into skin from bar soap with cationic polymer.

The test materials were the following bar soaps:

| | Test Soaps | | | | |
|---|---|---|---|---|---|
| | I | II | III | IV | V |
| Soap | 85.1 | 80.45 | 80.33 | 80.40 | 80.28 |
| Water | 13.5 | 13.5 | 13.5 | 13.5 | 13.5 |
| Fragrance | 1.0 | 1.0 | 1.0 | 1.0 | 1.0 |
| Glycerin | 0.4 | 5.0 | 5.0 | 5.0 | 5.0 |
| Vitamin E Acetate | 0 | 0.05 | 0.05 | 0.10 | 0.10 |
| Polyquaternium-6 | 0 | 0 | 0.12 | 0 | 0.12 |

The study was conducted using excised pig skin, a food-processing by-product. Baseline Vitamin E acetate levels in the skin were extracted with ethanol and analyzed by HPLC. The skin samples were then washed with the bar soaps. The wetted bars were applied for 15 seconds (by rubbing) and lather was generated for 45 seconds. The skin samples were rinsed with running tap water for 15 seconds and then air-dried.

Treated skin samples were extracted with ethanol ten minutes after treatment. The deposition of vitamins was determined by HPLC analysis and an average value of recovery±standard deviation was calculated based on all samples.

Deposition of Vitamin E Acetate as Picomoles/cm2

| Soap Sample Deposition | Vitamin E Acetate Mean ± SD |
|---|---|
| I. Control | 40 ± 2 |
| II. 5% Glycerin and 0.05% Vitamin E Acetate | 88 ± 4 |
| III. 5% Glycerin, 0.12%, Polyquat-6 and 0.05% Vitamin E Acetate | 130 ± 6 |
| IV. 5% Glycerin and 0.10% Vitamin E Acetate | 117 ± 2 |
| V. 5% Glycerin, 0.12% Polyquat-6 and 0.10% Vitamin E Acetate | 243 ± 9 |

The data in the above table demonstrate the excellent deposition brought about by a relatively small quantity of cationic polymer. The percent deposition of the Vitamin E acetate is increased substantially as the quantity of Vitamin E acetate is increased when cationic polymer is present.

EXAMPLE 2

A test was conducted to quantify the deposition of Vitamin E acetate into human skin from bar soap with cationic polymer.

The test products are the following:

| | Test Soaps | | | |
|---|---|---|---|---|
| | I | II | III | IV |
| Soap | 85.18 | 85.08 | 84.96 | 85.03 |
| Water | 13.50 | 13.50 | 13.50 | 13.50 |

-continued

| | Test Soaps | | | |
|---|---|---|---|---|
| | I | II | III | IV |
| Fragrance | 1.20 | 1.20 | 1.20 | 1.20 |
| Polyquaternium-6 | 0.12 | 0.12 | 0.24 | 0.12 |
| Vitamin E Acetate | 0 | 0.10 | 0.10 | 0.15 |

The study consisted of 9 days, 7 preconditioning days using bath and lotion products without Vitamin E or Vitamin E Acetate, followed by two test days. Twelve female volunteers between the ages of 18–55 participated in the study.

After the washout period, baseline Vitamin E Acetate levels in the skin were determined from panelists' forearms. Ethanol extractions of the skin surface were analyzed by HPLC.

Then, the forearms were washed with the bar soaps. The bars were applied for 15 seconds (by rubbing) to each forearm and lather generated for 45 seconds. The forearms were rinsed with running tap water for 15 seconds and then air-dried.

Treated skin was extracted with ethanol ten minutes after treatment.

Treated skin was extracted again at 5 hours and 24 hours after treatment.

The deposition of vitamins was determined by HPLC analysis, and an average value of recovery±standard deviation was calculated based on all the panelists.

| Deposition of Vitamin E Acetate (picomoles/cm2 +/− standard deviation) | | | |
|---|---|---|---|
| | Initial | 5 Hours | 24 Hours |
| I. Control | 6 ± 2 | 2 ± 2 | 4 ± 1 |
| II. 0.10% Vitamin E Acetate | 36 ± 5 | 21 ± 4 | 18 ± 2 |
| III. 0.10% Vitamin E Acetate with additional Polyquaternium-6 | 45 ± 5 | 43 ± 10 | 25 ± 5 |
| IV. 0.15% Vitamin E Acetate | 47 ± 5 | 42 ± 16 | 20 ± 4 |

The effect of additional cationic polymer is readily observed when comparing Example II to Example III. The additional cationic polymer of III brought about deposition of Vitamin E Acetate equivalent to the level obtained from raising the quantity of Vitamin E Acetate in the formulation by 50%, see IV.

What is claimed is:

1. A solid cleansing composition comprising a. About 5 to about 90 wt. % soap, b. About 0.01 to about 2.0 wt. % of Vitamin E Acetate, c. At least about 0.01 wt. % polyquat cationic deposition polymer, d. From zero to the essential absence of Vitamin E.

2. The composition in accordance with claim 1 wherein there is from 0 to about 0.05 wt. % of Vitamin E present.

3. The composition in accordance claim 1 wherein there is a minimum of about 60 wt. % soap.

4. The composition in accordance claim 1 wherein the polyquat is polyquat 6.

5. The composition in accordance claim 1 wherein there is less than 0.01 wt. % Vitamin E.

* * * * *